US00PP33019P2

(12) United States Plant Patent
van Dijk

(10) Patent No.: US PP33,019 P2
(45) Date of Patent: May 4, 2021

(54) *HYDRANGEA* PLANT NAMED 'HITOR'

(50) Latin Name: *Hydrangea macrophylla*
Varietal Denomination: HITOR

(71) Applicant: Roy Robin van Dijk, De Lier (NL)

(72) Inventor: Roy Robin van Dijk, De Lier (NL)

(73) Assignee: HI BREEDING B.V., De Lier (NL)

( * ) Notice: Subject to any disclaimer, the term of this patent is extended or adjusted under 35 U.S.C. 154(b) by 0 days.

(21) Appl. No.: 16/873,934

(22) Filed: Aug. 18, 2020

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Hydrangea* plant named 'HITOR', characterized by its upright and broadly spreading plant habit; freely branching habit; strong and sturdy stems; freely and reblooming flowering habit; large and dense inflorescences with medium to dark purplish red-colored sterile flowers; and good post-production longevity.

2 Drawing Sheets

Botanical designation: *Hydrangea macrophylla.*
Cultivar denomination: 'HITOR'.

STATEMENT REGARDING PRIOR DISCLOSURES BY INVENTOR/APPLICANT & ASSIGNEE

An European Community Plant Breeder's Rights application for the instant plant was filed by the Assignee, Hi Breeding B. V. of De Lier, The Netherlands, on Sep. 9, 2019, application number 2019/2203. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Hydrangea* plant, botanically known as *Hydrangea macrophylla*, commercially referred to as a mophead-type *Hydrangea* and hereinafter referred to by the name 'HITOR'.

The new *Hydrangea* plant is a product of a planned breeding program conducted by the Inventor in De Lier, The Netherlands. The objective of the breeding program is to create new sturdy and strong *Hydrangea* plants with attractive inflorescences and good postproduction longevity.

The new *Hydrangea* plant originated from a cross-pollination in March, 2013 of a proprietary selection of *Hydrangea macrophylla* identified as code number 1216, not patented, as the female, or seed, parent with a proprietary selection of *Hydrangea macrophylla* identified as code number 1335, not patented, as the male, or pollen, parent. The new *Hydrangea* plant was discovered and selected as a single flowering plant from within the progeny of the stated cross-pollination in a controlled greenhouse environment in De Lier, The Netherlands in April, 2015.

Asexual reproduction of the new *Hydrangea* plant by terminal vegetative cuttings since June, 2016 in a controlled greenhouse environment in De Lier, The Netherlands has shown that the unique features of this new *Hydrangea* plant are stable and reproduced true to type in successive generations of asexual reproduction.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HITOR'. These characteristics in combination distinguish 'HITOR' as a new and distinct *Hydrangea* plant:

1. Upright and broadly spreading plant habit.
2. Freely branching habit.
3. Strong and sturdy stems.
4. Freely flowering habit.
5. Large and dense inflorescences with medium to dark purplish red-colored sterile flowers.
6. Good post-production longevity.

Plants of the new *Hydrangea* can be compared to plants of the female parent selection. Plants of the new *Hydrangea* differ primarily from plants of the female parent selection in the following characteristics:

1. Plants of the new *Hydrangea* are more compact than and not as vigorous as plants of the female parent selection.
2. Stems of plants of the new *Hydrangea* are sturdier than stems of plants of the female parent selection.
3. Sterile flower sepals of plants of the new *Hydrangea* are darker purplish red in color than sterile flower sepals of plants of the female parent selection.

Plants of the new *Hydrangea* can be compared to plants of the male parent selection. Plants of the new *Hydrangea* differ primarily from plants of the male parent selection in the following characteristics:

1. Plants of the new *Hydrangea* are more compact than plants of the male parent selection.
2. Stems of plants of the new *Hydrangea* are sturdier than stems of plants of the male parent selection.

Plants of the new *Hydrangea* can also be compared to plants of *Hydrangea macrophylla* 'Hot Red', not patented. In side-by-side comparisons, plants of the new *Hydrangea* differed primarily from plants of 'Hot Red' in the following characteristics:

1. Plants of the new *Hydrangea* are not as compact as and are more vigorous than plants of 'Hot Red'.
2. Stems of plants of the new *Hydrangea* are more sturdy than stems of plants of 'Hot Red'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet is a side perspective view of a typical flowering plant of 'HITOR' grown in a container.

The photograph at the top of the second sheet is a close-up view of a typical inflorescence of 'HITOR', and the photograph at the bottom of the second sheet is a close-up view of typical leaves of 'HITOR'.

DETAILED BOTANICAL DESCRIPTION

Plants used in the aforementioned photographs and in the following description were grown during the autumn in 14-cm containers in a glass-covered greenhouse in De Lier, The Netherlands and under cultural practices typical of commercial *Hydrangea* production. During the production of the plants, day temperatures ranged from 20° C. to 35° C., night temperatures ranged from 10° C. to 22° C. and lightly levels were about 4,000 lux for 16 hours per day. Plants of the new *Hydrangea* were pinched one time and were two years old when the photographs and description were taken. In the following description, color references are made to The Royal Horticultural Society Colour Chart, 2015 Edition, except where general terms of ordinary dictionary significance are used. Plants are not typically "blued" (treated with aluminum sulfate).

Botanical description: *Hydrangea macrophylla* 'HITOR'.

Parentage:

*Female, or seed, patent*.—Proprietary selection of *Hydrangea macrophylla* identified as code number 1216, not patented.

*Male, or pollen, patent*.—Proprietary selection of *Hydrangea macrophylla* identified as code number 1335, not patented.

Propagation:

*Type cutting*.—By vegetative terminal cuttings.

*Time to initiate roots, summer*.—About twelve days at temperatures about 22° C.

*Time to initiate roots, winter*.—About two weeks at temperatures about 20° C.

*Time to produce a rooted young plant, summer*.—About four weeks at temperatures about 22° C.

*Time to produce a rooted young plant, winter*.—About 30 days at temperatures about 19° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Upright, broadly outwardly spreading and mounding plant habit; flattened globular in overall shape; strong and sturdy stems; moderately vigorous growth habit and moderate growth rate; about six months from propagation are required to produce a finished flowering plant.

*Plant height*.—About 31.3 cm.

*Plant diameter or area of spread*.—About 54.3 cm.

Lateral branch description:

*Branching habit*.—Freely branching habit with about eleven lateral branches per plant; pinching is not required, but will enhance lateral branch development.

*Length*.—About 14.9 cm.

*Diameter*.—About 5 mm.

*Internode length*.—About 3.9 cm.

*Strength*.—Strong, sturdy.

*Aspect*.—About 55° from vertical.

*Texture*.—Smooth, glabrous; fully developed, woody.

*Color, developing*.—Close to 144B.

*Color, fully developed*.—Close to 144A, at the internodes, slightly tinged with close to N186C; woody, close to 199B and 199C and N199D.

*Lenticels*.—Density: Sparse to medium. Length: About 2 mm. Width: About 0.5 mm. Color: Close to N186C.

Leaf description:

*Arrangement*.—Opposite, simple.

*Length*.—About 11.3 cm.

*Width*.—About 7.6 cm.

*Shape*.—Broadly ovate to broadly elliptic.

*Apex*.—Apiculate.

*Base*.—Short attenuate.

*Margin*.—Coarsely serrate.

*Texture and luster, upper surface*.—Slightly rugose, glabrous; glossy.

*Texture and luster, lower surface*.—Moderately rugose, glabrous; somewhat glossy.

*Venation pattern*.—Pinnate.

*Color*.—Developing leaves, upper surface: Close to 143A. Developing leaves, lower surface: Close to between 143B and 144A. Fully developed leaves, upper surface: Darker than between NN137A and 147A; venation, close to 146C. Fully developed leaves, lower surface: Close to between 146B and 147B; venation, close to 146D.

*Petioles*.—Length: About 2.2 cm. Diameter: About 4.5 mm. Texture and luster, upper and lower surfaces: Smooth, glabrous; slightly glossy. Color, upper surface: Close to 144A. Color, lower surface: Close to 144B.

Flower description:

*Flower type and habit*.—Showy rotate sterile flowers and small, inconspicuous rotate fertile flowers arranged on mophead-type terminal panicles; panicles flattened globular in shape; sterile flowers face upright to outwardly, and fertile flowers mostly upright.

*Fragrance*.—None detected.

*Natural flowering season*.—In the garden, plants flower continuously from the late spring to late summer in The Netherlands.

*Flower longevity*.—Good postproduction longevity; sterile flowers maintain good substance for about six weeks on the plant, sterile flowers persistent; fertile flowers last about three days on the plant, fertile flowers not persistent.

*Quantity of flowers*.—Freely flowering habit; about 120 sterile flowers per panicle and about 30 fertile flowers per panicle.

*Panicle height*.—About 10.3 cm.

*Panicle diameter*.—About 16.3 cm.

*Sterile flower buds*.—Length: About 1 cm. Diameter: About 1.9 cm. Shape: Broadly cup-shaped. Color: Close to 67A.

*Fertile flower buds*.—Length: About 4 mm. Diameter: About 3.5 mm. Shape: Flattened globular. Color: Close to 147D; distally, close to 144B and proximally, close to 144C.

*Sterile flower diameter*.—About 4.2 cm.

*Sterile flower depth* (*height*).—About 1.2 cm.

*Fertile flower diameter*.—About 8 mm.

*Fertile flower depth* (*height*).—About 7 mm.

*Petals, sterile flowers*.—Quantity and arrangement: Four in a single whorl. Length: About 2.5 mm. Width: About 1.5 mm. Shape: Broadly ovate, moderately concave. Apex: Acute. Base: Cuneate. Margin: Entire. Texture and luster, upper and lower surfaces: Smooth, glabrous; matte. Color: When opening and fully opened, upper surface: Close to 70B; color does not change with development. When opening and fully opened, lower surface: Close to 68B; color does not change with development.

*Petals, fertile flowers*.—Quantity and arrangement: Five in a single whorl. Length: About 3.5 mm. Width: About 2 mm. Shape: Ovate, concave. Apex: Acute. Base: Cuneate. Margin: Entire. Texture and luster, upper and lower surfaces: Smooth, glabrous; matte. Color: When opening and fully opened, upper surface: Center, close to N77B; towards the apex, base and margin, close to N155B; colors do not change with development. When opening and fully opened, lower surface: Close to 145D; towards the base, tinged with close to N75D; colors do not change with development.

*Sepals, sterile flowers*.—Quantity and arrangement: Typically four or five in a single whorl. Length: About 2.2 cm. Width: About 2.1 cm. Shape: Broadly rhomboidal to close to deltoid. Apex: Broad and bluntly acute. Base: Broadly cuneate. Margin: Entire; moderately and coarsely undulate. Texture and luster, upper and lower surfaces: Smooth, glabrous; matte. Color: When opening, upper surface: Close to 61C. When opening, lower surface: Close to 64D. Fully opened, upper surface: Close to between 58A and 61B; with development, colors becoming closer to 178B and 178C strongly tinged with 146A. Fully opened, lower surface: Close to 70C; with development, colors becoming closer to 180D and 181D tinged with 148D.

*Sepals, fertile flowers*.—Quantity and arrangement: Five in a single whorl. Length: About 3.5 mm. Width: About 2 mm. Shape: Broadly ovate. Apex: Bluntly acute to acute. Base: Broadly cuneate. Margin: Entire. Texture and luster, upper and lower surfaces: Smooth, glabrous; matte. Color: When opening, upper surface: Close to 143A. When opening, lower surface: Close to 144B. Fully opened, upper surface: Close to 143A; towards the base, tinged with close to 58D; color does not change with development. Fully opened, lower surface: Close to 144A to 144B; towards the base, tinged with close to 58D and lighter than 58D; color does not change with development.

*Pedicels, sterile flowers*.—Length: About 2.4 cm. Diameter: About 1.25 mm. Strength: Moderately strong. Aspect: About 40° from peduncle. Texture and luster: Moderately pubescent; matte. Color: Close to 181D.

*Pedicels, fertile flowers*.—Length: About 5 mm. Diameter: About 1 mm. Strength: Moderately strong. Aspect: About 10° from peduncle. Texture and luster: Smooth, glabrous; matte. Color: Close to 145A tinged with close to 75C.

*Reproductive organs, sterile flowers*.—Stamens: Quantity per flower: Eight. Filament length: About 3.5 mm. Filament color: Close to 65C to 65D. Anther length: About 0.75 mm. Anther shape: Broadly oblong. Anther color: Close to 155D. Pollen amount: Moderate. Pollen color: Close to 155A. Pistils: Pistil quantity per flower: Two or three. Pistil length: About 1.5 mm. Stigma shape: Club-shaped. Stigma color: Close to 75D. Style length: About 1 mm. Style color: Close to 73B to 73C. Ovary color: Close to N155C.

*Reproductive organs, fertile flowers*.—Stamens: Quantity per flower: Ten. Filament length: About 3.5 mm. Filament color: Close to 65C to 65D. Anther shape: Broadly oblong. Anther length: About 0.75 mm. Anther color: Close to 155D. Pollen amount: Moderate. Pollen color: Close to 155A. Pistils: Pistil quantity per flower: Two or three. Pistil length: About 1.5 mm. Stigma shape: Club-shaped. Stigma color: Close to 75D. Style length: About 1 mm. Style color: Close to 73B to 73C. Ovary color: Close to 145C.

*Seeds*.—To date, seed development has not been observed on plants of the new *Hydrangea*.

Pathogen & pest resistance: Under commercial production conditions, plants of the new *Hydrangea* have been observed to tolerate Powdery Mildew (*Erysiphe friesii* var. *friesii*) and *Botrytis* (*Botrytis cinerea*). Plants of the new *Hydrangea* not been observed to be resistant to pests and other pathogens common to *Hydrangea* plants.

Temperature tolerance: Plants of the new *Hydrangea* have been shown to be suitable for USDA Hardiness Zones 5 through 9.

It is claimed:

1. A new and distinct *Hydrangea* plant named 'HITOR' as illustrated and described.

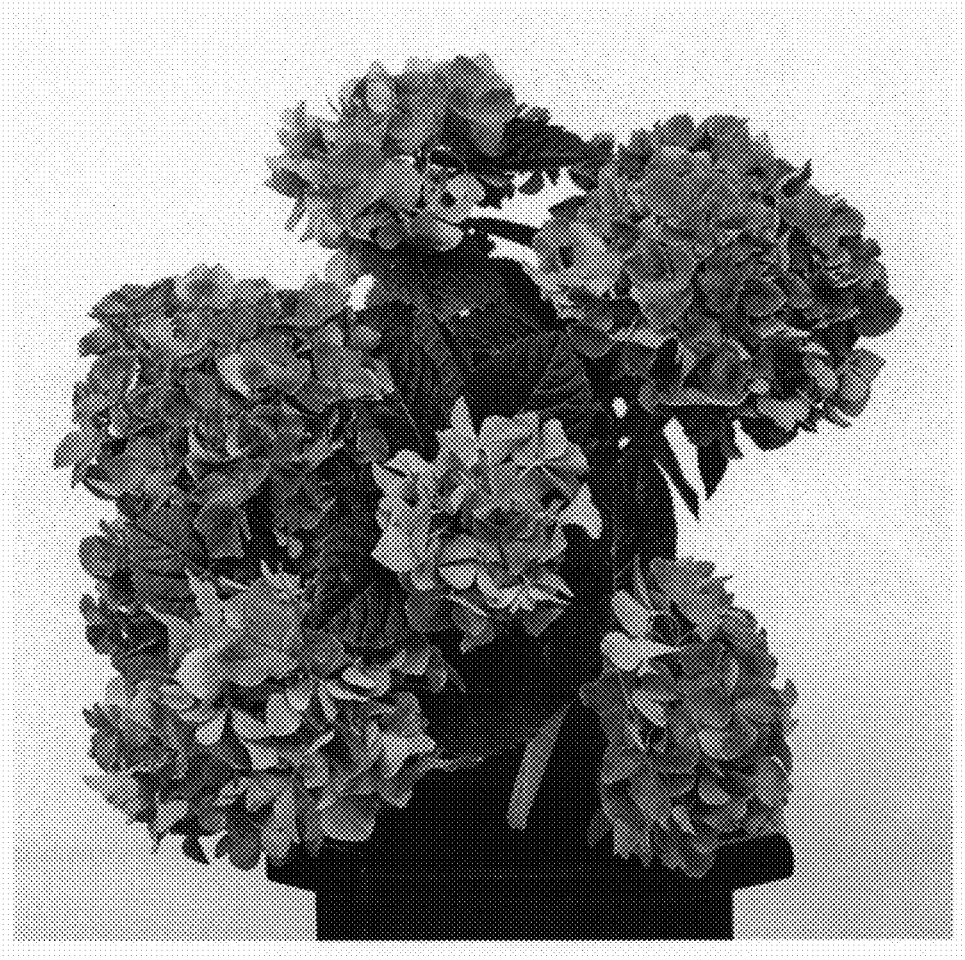

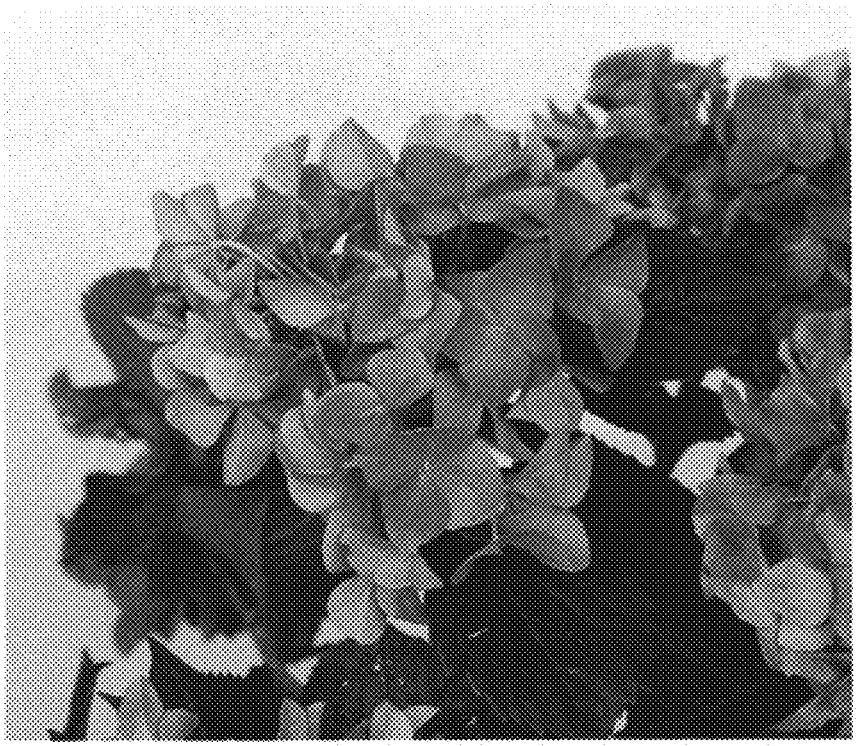
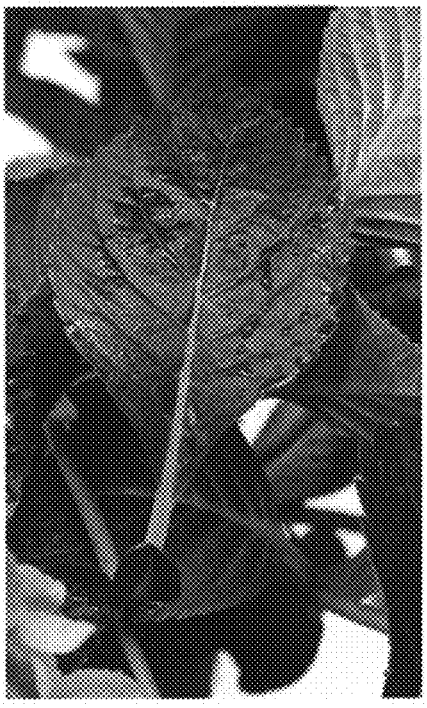

* * * * *